(12) United States Patent
Haskell et al.

(10) Patent No.: US 7,437,302 B2
(45) Date of Patent: Oct. 14, 2008

(54) SYSTEM FOR MANAGING HEALTHCARE RELATED INFORMATION SUPPORTING OPERATION OF A HEALTHCARE ENTERPRISE

(75) Inventors: Robert Emmons Haskell, Chester Springs, PA (US); Gary Hardel, Wayne, PA (US); Harold Kenneth Shumaker, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1043 days.

(21) Appl. No.: 10/253,310

(22) Filed: Sep. 24, 2002

(65) Prior Publication Data

US 2003/0078813 A1    Apr. 24, 2003

Related U.S. Application Data

(60) Provisional application No. 60/337,778, filed on Oct. 22, 2001.

(51) Int. Cl.
*G06Q 10/00* (2006.01)
(52) U.S. Cl. .............................................. 705/2; 705/3
(58) Field of Classification Search .................. 705/2–3
See application file for complete search history.

(56) References Cited

U.S. PATENT DOCUMENTS

| | | | | |
|---|---|---|---|---|
| 5,560,005 | A | * | 9/1996 | Hoover ......................... 707/10 |
| 5,664,109 | A | * | 9/1997 | Johnson et al. ................. 705/2 |
| 5,915,241 | A | * | 6/1999 | Giannini ........................ 705/2 |
| 5,991,728 | A | | 11/1999 | DeBusk et al. ................. 705/2 |
| 6,014,629 | A | * | 1/2000 | DeBruin-Ashton ............ 705/2 |
| 6,067,548 | A | | 5/2000 | Cheng ......................... 707/103 |
| 6,072,493 | A | | 6/2000 | Driskell et al. ............... 345/356 |
| 6,182,029 | B1 | * | 1/2001 | Friedman ........................ 704/9 |
| 6,223,164 | B1 | | 4/2001 | Seare et al. ..................... 705/2 |

(Continued)

FOREIGN PATENT DOCUMENTS

EP    1 304 645 A    4/2003

OTHER PUBLICATIONS

Gennari et al., "A Web-Based Architecture for a Medical Vocabulary Server", Ninteenth Annual Symposium on Computer Applications in Medical Care, 1995, pp. 275-279.*

(Continued)

*Primary Examiner*—Vanel Frenel
(74) *Attorney, Agent, or Firm*—Alexander Burke

(57) ABSTRACT

A comprehensive database system employs common medical terms, vocabularies and identifiers in identifying organizational characteristics as well as location availability and suitability for delivering services by a particular physician to a patient with particular medical conditions via a user friendly display interface. A system for managing healthcare data including codes, terms and identifiers supports operation of a healthcare enterprise. The system includes a first database including healthcare data including elements common to a plurality of healthcare organizations and derived from a plurality of different sources. The healthcare data common elements support use of consistent terminology between the plurality of organizations. A processor provides at least a portion of the healthcare data in the first database to a second database employed by at least one of the plurality of organizations in response to user command. The second database also supports use of user selectable items of healthcare data. An interface processor intermittently receives healthcare data updates for incorporation in the first database.

12 Claims, 8 Drawing Sheets

U.S. PATENT DOCUMENTS

| | | | |
|---|---|---|---|
| 6,311,192 B1 | 10/2001 | Rosenthal et al. | 707/200 |
| 6,314,556 B1 | 11/2001 | Debusk et al. | 717/1 |
| 6,397,224 B1* | 5/2002 | Zubeldia et al. | 707/102 |
| 2001/0037227 A1 | 11/2001 | McInnis et al. | 705/7 |
| 2001/0041992 A1* | 11/2001 | Lewis et al. | 705/3 |
| 2002/0016923 A1* | 2/2002 | Knaus et al. | 713/200 |
| 2002/0018066 A1 | 2/2002 | Vizer | 345/428 |
| 2002/0059201 A1 | 5/2002 | Work | 707/3 |
| 2002/0059251 A1 | 5/2002 | Stern et al. | 707/10 |
| 2002/0128871 A1* | 9/2002 | Adamson et al. | 705/3 |
| 2003/0074225 A1* | 4/2003 | Borsand et al. | 705/3 |
| 2003/0078911 A1 | 4/2003 | Haskell | |
| 2005/0027566 A1 | 2/2005 | Haskell | |

OTHER PUBLICATIONS

Oliver et al., "Development of a Change Model for a Controlled Medical Vocabulary", 1997 Annual Fall Symposium AMIA, 1997, 6 pages.*

Bakken et al., "Evaluation of the Clinical LOINC (Logical Observation Identifiers, Names, Codes) Semantic Structure as a Terminology Model for Standardized Assessment Measures", Journal of AMIA, Dec. 2000, vol. 7, No. 6, pp. 529-538.*

A Web Based Architecture for a Medical Vocabulary Server by Gennari et al; pp. 1-5.*

Signature Product description information Jun. 1985.

Structuring the Observatory Data.

Health Supplier http://www.healthtrade.com.tw/en/left/healthsupplier-en.htm.

Organization Profile (OP FORM): http://www.unece.org/ceiproj/ex1op.htm.

HelathCare informatics: February 199 News and Trends http://www.health-.

Who needs a standard medical terminology . . . Kim Batch Enterprise Architect Center for Biomedical.

Michael A. Hogarth et al. terminology Query Language: A Server Interface for concept-Oriented.

Apelon Products http://www.apelon.com/products/products . . . authoring.htm.

SMS "Common Vocabulary Engine" Jul. 1999 Soarian Knows, System Architecture Siemens Medical.

"Siemens Reference Architecture Overview" Siemens Aug. 2003.

International Search Report.

Ingenerf J et al.: "Standardized terminological services enabling semantic interoperability between distributed and heterogeneous systems" International Journal of Medical Informatics, Elsevier Scientific Publishers, Shannon, IR, vol. 64::Dec. 2-3, 2001 pp. 223-240 XP004329213 ISSN: 1386-5056.

Elkin P L et al: "Automated enhancement of description logic-defined terminologies to facilitate mapping to ICD9-CM" Journal of Biomedical Informatics Academic Press USA, vol. 35:Oct. 5-6, 2002 pp. 281-288, XP002330230 ISSN: 1532-0464.

Bechhofer S K et al: "Terminologies and terminology servers for information environments" Software Technology and Engineering Practice, 1997, Proceedings., Eighth IEEE International Workshop on Incorporating Computer Aided Software Engineering London, UK Jul. 14-18, 1997, Los Alamitos, CA USA, IEEE Comput. Soc, US, Jul. 14, 1997 pp. 484-497 XP010240938 ISBN: 0-8186-7840-2.

Rector A L et al.: "A Terminology Server for Medical Language and Medical Information Systems" International Medical Informatics Association, WG 6 Working Conference, May 1994 pp. 1-16, XP002330229.

Nikolai R et al.: "Thesaurus federations: a framework for the flexible integration of heterogeneous, autonomous thesauri" Research and Technology Advances in Digital Libraries, 1998, ADL 98, Proceedings. IEEE International Forum on Santa Barbara, CA USA Apr. 22-24, 1998, Los Alamitos, CA, USA IEEE Comput. Soc, US, Apr. 22, 1998 pp. 46-55 XP010276876 ISBN: 0-8186-8464-X.

Yu H et al: "Representing Genomic Knowledge in the UMLS Semantic Network" AMIA Annual Symposium. A Conference of the American Medical Informatics Association. Proceedings. Proceedings of AMIA Annual Symposium the Emergence of Internetable Health Care Systems That Really Work, Nov. 6, 1999 pp. 181-185, XP002207393.

Lowe J H et al: "The Image Engine HPCC Project. A Medical digital library system using agent-based technology to create an integrated view of the electronic medical record" Digital Libraries, 1996. ADL 1996, Proceedings of the Third Forum on Research and Technology Advances in Washington, DC, USA May 13-15, 1996, Los Alamitos, CA USA, IEEE Comput. Soc, US, May 13, 1996 pp. 45-56, XP010164909.

* cited by examiner

Find a location

Search by:

Location Name: [3] ▶ □ Exact match — 902

Category: [Patient location] ▶ — 904

Type: ▶ — 906

Service provider organization: ▶ — 908

Clinical service: ▶ — 910

□ Main □ Primary □ Secondary

Gender designation — 913
- ⦿ None
- ○ For female patients only
- ○ For male patients only

Results: (108 found - you might want to narrow your criteria) — 920

| Location name | ORG-BAY HOSPITAL | Type |
|---|---|---|
| 3West Pre-op | | Ward |
| 3West Recovery | | Ward |
| 3West Surgery | | Ward |
| 301 | | Private room |
| 302A | | Bed |
| 302B | | Bed |
| 303A | | Bed |
| 303B | | Bed |
| 304A | | Bed |
| 304B | | Bed |
| 305A | | Bed |
| 305B | | Bed |
| 306 | | Private room |
| 307A | | Bed |
| 307B | | Bed |

Details: — 923

304A
Max. 1 occupant(s)
Normal level/care: Xxxxxx
Clinical services: Med/Surg, Orthopedics, Oncology

[⚙ Go search] — 925   [⚙ Clear search]   🔍   [Add new]   [Cancel]

| | HEALTH PROVIDER ORGANIZATION | LOCATION | HEALTH PROFESSIONAL | HEALTH SERVICE | MEDICAL CLASSIFICATION | PAYER | INSURANCE PLAN |
|---|---|---|---|---|---|---|---|
| HEALTH PROVIDER ORGANIZATION | | OWNS OWNED BY AFFILIATES WITH | OWNS AFFILIATES WITH | OWNS AFFILIATES WITH | AFFILIATES WITH | AFFILIATES WITH | OWNS AFFILIATES WITH |
| LOCATION | OWNS OWNED BY AFFILIATES WITH | | AFFILIATES WITH | OWNS AFFILIATES WITH | AFFILIATES WITH | | AFFILIATES WITH |
| HEALTH PROFESSIONAL | OWNED BY AFFILIATES WITH | OWNS OWNED BY | | AFFILIATES WITH | AFFILIATES WITH | | AFFILIATES WITH |
| HEALTH SERVICE | OWNED BY AFFILIATES WITH | AFFILIATES WITH | OWNS OWNED BY AFFILIATES WITH | | AFFILIATES WITH | | AFFILIATES WITH |
| MEDICAL CLASSIFICATION | OWNED BY AFFILIATES WITH | AFFILIATES WITH | AFFILIATES WITH | AFFILIATES WITH | | | AFFILIATES WITH |
| PAYER | AFFILIATES WITH | AFFILIATES WITH | AFFILIATES WITH | AFFILIATES WITH | OWNS OWNED BY AFFILIATES WITH | | OWNS |
| INSURANCE PLAN | AFFILIATES WITH | | | | | OWNED BY | |
| | OWNED BY AFFILIATES WITH | AFFILIATES WITH | AFFILIATES WITH | AFFILIATES WITH | AFFILIATES WITH | OWNED BY | OWNS OWNED BY AFFILIATES WITH |

…

SYSTEM FOR MANAGING HEALTHCARE RELATED INFORMATION SUPPORTING OPERATION OF A HEALTHCARE ENTERPRISE

This is a non-provisional application of provisional application Ser. No. 60/337,778 by R. E. Haskell et al. filed Oct. 22, 2001. This application is concurrently filed together with commonly owned related application entitled, A System for Providing Healthcare Related Information, Ser. No. 10/252,972 filed Sep. 23, 2002.

FIELD OF THE INVENTION

This invention concerns a system and user interface for processing organization, location, service and associated information including codes, terms identifiers, business rules and mapping information for use in supporting healthcare or other organization operation, for example.

BACKGROUND OF THE INVENTION

Healthcare related enterprises have grown rapidly through the acquisition of, and affiliation with, other organizational entities, creating a "multientity" health system. Tight operational integration of these entities has proved to be problematic, and affiliation is now the preferred model. In this way they have the benefit of enhanced leverage with external stakeholders (e.g., managed care organizations, suppliers) as well as the autonomy to deal with parochial issues. The result is an enterprise that is often organizationally, culturally, methodologically, geographically, and technologically diverse and fragmented. A challenge for this diverse, fragmented, multi-entity healthcare enterprise is to serve its customers through a seamlessly integrated continuum of services. A challenge for a software vendor is to provide software to support the multi-entity healthcare enterprise in delivering a seamlessly integrated continuum of services. The ability to deliver such seamless integration depends to a large degree on being able to share data between the constituent organizations of the multi-entity healthcare enterprise. This is impeded by the use of different terms, medical and other vocabularies and identifiers by the different constituent organizations.

The multi-entity healthcare enterprise is also required to employ many health-care workers to provide services to patients at a multiplicity of locations and involves a corresponding multiplicity of organizations (e.g. companies, payers, institutions, physician practices, clinics, hospitals, pharmacies etc.). Further, healthcare operations are structured into specialized departments such as nursing, laboratory, radiology, pharmacy, surgery, emergency, administrative and other departments which are variously located at one or more sites and may be associated with different organizations. The management of organization and location and related information involves accumulating, processing and maintaining large quantities of information. This information is employed in determining organizational relationships, including affiliations and characteristics as well as location availability and suitability for delivering services by a particular physician to a patient with particular medical conditions. The information also supports provision of clinical care, patient tracking, billing and administration and other purposes. Consequently, there is a need for a computerized system capable of defining and maintaining organization, location, service, physician, payer and insurance information as well as supporting sharing this information between different entities. It is also desirable that such a system supports sharing the maintained information between entities employing different terms, medical and other vocabularies and identifiers. A system according to invention principles addresses the identified deficiencies and derivative problems.

SUMMARY OF INVENTION

A comprehensive database system employs common medical terms, vocabularies and identifiers in identifying organizational characteristics as well as location availability and suitability for delivering services by a particular physician to a patient with particular medical conditions via a user friendly display interface. A system for managing healthcare data including codes, terms and identifiers supports operation of a healthcare enterprise. The system includes a first database including healthcare data including elements common to a plurality of healthcare organizations and derived from a plurality of different sources. The healthcare data common elements support use of consistent terminology between the plurality of organizations. A processor provides at least a portion of the healthcare data in the first database to a second database employed by at least one of the plurality of organizations in response to user command. The second database also supports use of user selectable items of healthcare data. An interface processor intermittently receives healthcare data updates for incorporation in the first database.

BRIEF DESCRIPTION OF THE DRAWING

FIG. 5 shows a user interface display image menu supporting a user search for organization, location and service information using centrally maintained common codes, terms and identifiers, according to invention principles.

FIG. 9 shows a table indicating structural relationships between objects maintained by the central repository database (and distributed repository databases) of the system of FIG. 1, according to invention principles.

DETAILED DESCRIPTION OF INVENTION

Figure 1:
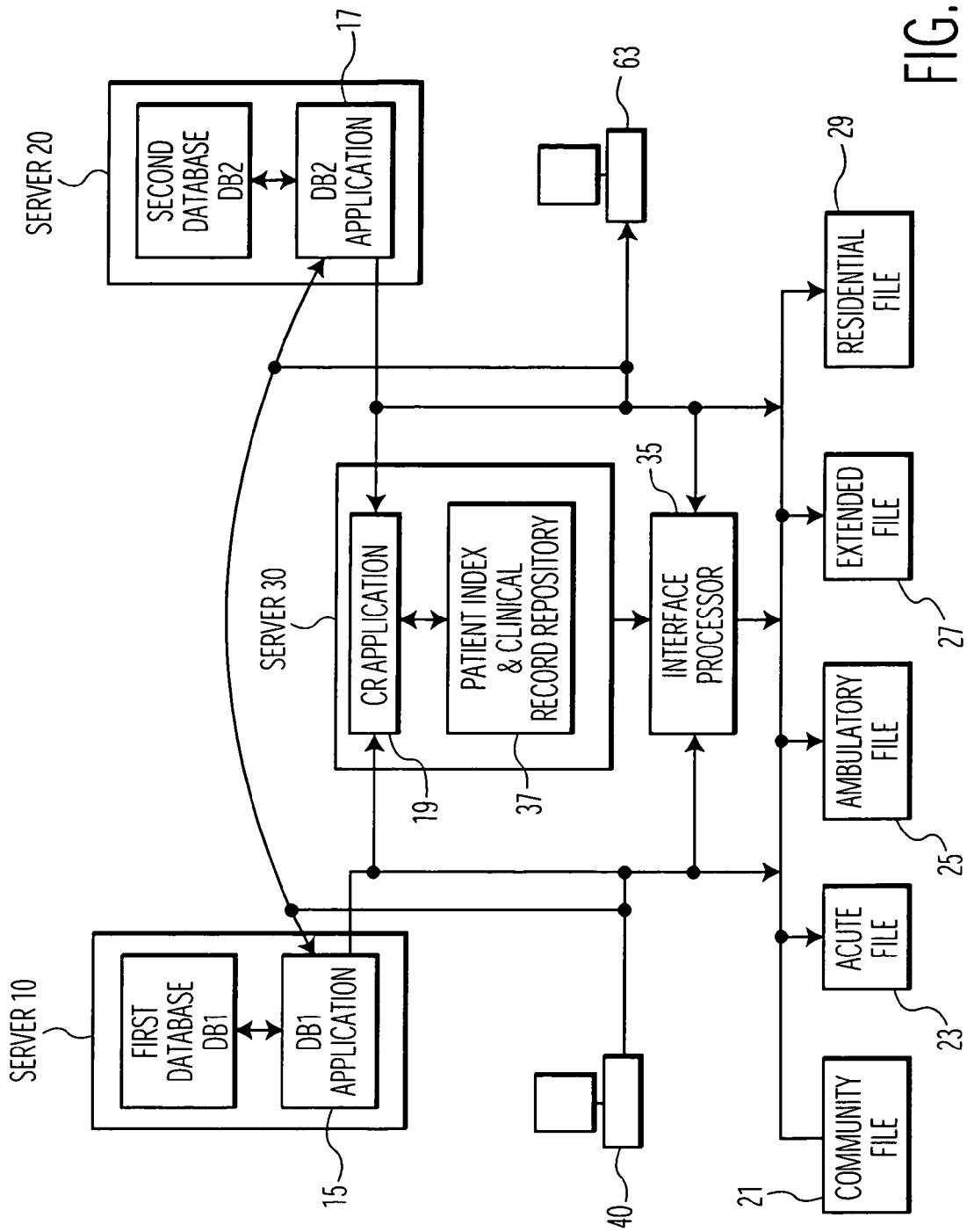
FIG. 1 shows a system for managing healthcare related information supporting operation of a healthcare enterprise, according to invention principles.

FIG. 1 shows a system for managing healthcare related information supporting operation of a healthcare enterprise. In the FIG. 1 system database management application 15 manages access to database DB1 on server 10. DB1 acts as a central repository of information supporting terminology consistency and operation of a health network encompassing multiple constituent organizations. The information enables operation and documentation of both clinical and business processes and their interaction. Such interaction is involved in determining whether a proposed treatment meets health plan medical necessity requirements, or in determining health plan coverage rules for a particular treatment, or to define business policy or best practices, for example. The terminology, including vocabularies, code sets and identifiers, is employed in characterizing or identifying a health provider organization, a location in an organization, a healthcare worker, a medical condition, a Health service, a payer organization, or a particular health plan. DB1 contains medical terms, vocabularies and identifiers in addition to organizational characteristics as well as location and other information supporting identification of location availability and suitability in a particular organization for delivering services by a particular physician to a patient with a particular medical condition. A medical code set as used herein is any set of codes used for encoding data elements, such as tables of terms, medical concepts, medical diagnosis codes, or medical procedure codes. DB1 also contains payer, health service and health plan information facilitating the billing and financial operations involved in delivering healthcare to a patient. This information is structured and linked within DB1 using known indexing and associative methods to facilitate information, access, update and output communication to information requesting applications.

Application 15 intermittently distributes information from the central repository DB1 to repositories of constituent organizations of a health network such as to repository DB2 via a DB2 database management application 17 residing on server 20. Application 15 also intermittently distributes information from the central repository DB1 to a clinical record management application 19 supporting a master patient index and associated clinical records in repository 37 residing on server 30. The information distribution may be initiated periodically, upon detection of a change in stored data, or upon an update request or command from a requesting application or in response to an information update cycle or as determined by user need or another indication that a target repository is to be updated. Information from DB1 and DB2 as well as from the clinical record and patient index repository 37 is used in compiling data files for particular uses involved in managing the healthcare system operation. Such files may include a file 21 of healthcare data for a particular community of patients, a file 23 of healthcare data supporting one or more acute care facilities, a file 25 of healthcare data for patients identified as being ambulatory, a file 27 of extended data beyond that found in a clinical record and a file 29 of healthcare data concerning patients receiving residential care, for example. The data used to compile these files may be derived directly from DB1, DB2 and repository 37 via applications 15, 17 and 19 respectively or this data may be structured and formatted by interface processor 35 in compiling the files. Information is also intermittently transferred from repositories of constituent organizations of a health network such as from repository DB2 via application 17 to the central record repository DB1 or the clinical record repository 37 or other organization repositories (not shown to preserve drawing clarity). Information provided from DB2 may include terminology, vocabularies, identifiers, business rules, organization data, location information and other information used within the local healthcare organization, for example. Further, personal computers (PCs) 40 and 63 may be used for searching, processing and presenting healthcare related information to a user from DB1 via application 15 and from DB2 via application 17 respectively.

The information is structured and linked within DB1 (and DB2) as vocabulary "objects" and an individual vocabulary object has a corresponding set of attributes. Vocabulary object attributes may include identifiers, health provider organization data as well as business rules and synonyms. The identifiers may be used for identification of health provider organizations, healthcare workers, medical classifications, and payer organizations as well as patients. A particular health provider organization object is linked to other objects within DB1 to establish an ownership, responsibility chain or affiliation of the other objects to a particular constituent organization of an encompassing health network. This ownership type relationship extends to constituent organizations of the particular health provider organization so that these constituent organizations use the same consistent set of vocabulary objects. However, medical classification object data may be an exception. A particular constituent organization may be identified as using a particular subset of medical conditions and associated classification codes. This type of exception is identified and managed by application 15 in intermittently transferring DB1 information to a DB2 repository of the particular constituent organization.

The DB1 vocabulary object attributes include business rules and associated constraints. Rules associated with a health worker may determine if a physician is limited to a specialty or is board certified, for example. Constraints associated with a location may determine whether a room is restricted to VIP use, for example. Rules associated with a health service may determine if a consultation is required or whether pre-authorization of a medical procedure is required, or whether restricted access is to be applied to particular test results (such as an HIV result or a psychiatric assessment), for example. Further, the DB1 vocabulary object attributes include synonyms for use in mapping a term, code or identifier used by a first constituent organization to a corresponding different term, code or identifier used by a second constituent organization. This mapping may also map sets of codes, terms and identifiers and supports data exchange and interaction between health provider organizations with different vocabularies, for example.

The linked vocabulary objects within DB1 (and DB2) include health provider organization characteristics as well as location characteristics. The linked objects also include healthcare workers (e.g. a physician) and associated characteristics (e.g. specialty), medical condition, a health service, a payer organization and health plan and other objects. The objects are grouped in ownership hierarchies (e.g., health services are grouped with other services and are associated with goods and service order sets and protocols). The DB1 structure identifies hierarchically associated locations (e.g., containing other locations) as well as those health professionals that may be authorized to perform certain health services and the particular health services that are performable at certain locations. The DB1 structure also indicates whether a health plan may authorize certain health provider organizations and health professionals to perform certain health services, if appropriate for a given medical condition.

FIG. 9 shows a table indicating structural relationships between objects maintained by the central repository database DB1 (and distributed repository database DB2) of the system of FIG. 1. The DB1 structure maintains complex relationships between objects including a health provider organization 900, a location in a constituent organization 903, a health professional 905, a health service 907, a medical condition code or classification 909, a payer organization 911 and a health plan 913 and other objects. Such other objects include codes, terms and identifiers and mapping information and business rules as well as location and organization characteristics. The types of relationships are illustrated in FIG. 9 and include ownership and affiliation relationships between objects listed in the lead row and lead column. A health provider organization may own other constituent health provider organizations or may own or be affiliated with a location, for example. The DB1 objects may comprise multiple hierarchies or sets of objects (e.g., service sets, health professional roles, or matrix structured product line organizations). Further, an affiliation type relationship between objects may comprise a non-exclusive, non-hierarchical relationship. Internal identifiers are used within DB1 to identify an object and a relationship, however in other embodiments objects and relationships may be identified by predetermined structural location or indices, for example, as known in database technology.

The central repository DB1 of the system of FIG. 1 advantageously provides a single point of maintenance and control for codes, terms and identifiers as well as organization, location, payer, health professional, health plan and service data. The system also readily adapts to accommodate installation of new applications, changes in organization structure, creation of a patient index and electronic patient record repository. The central repository DB1 enables constituent organizations of a health network to use consistent codes terms and identifiers derived from local, national and international sources and acts as a source of template starter sets of terms for distributed databases such as DB2. The system further supports use of local or proprietary terms by a particular constituent organization.

Figure 2:
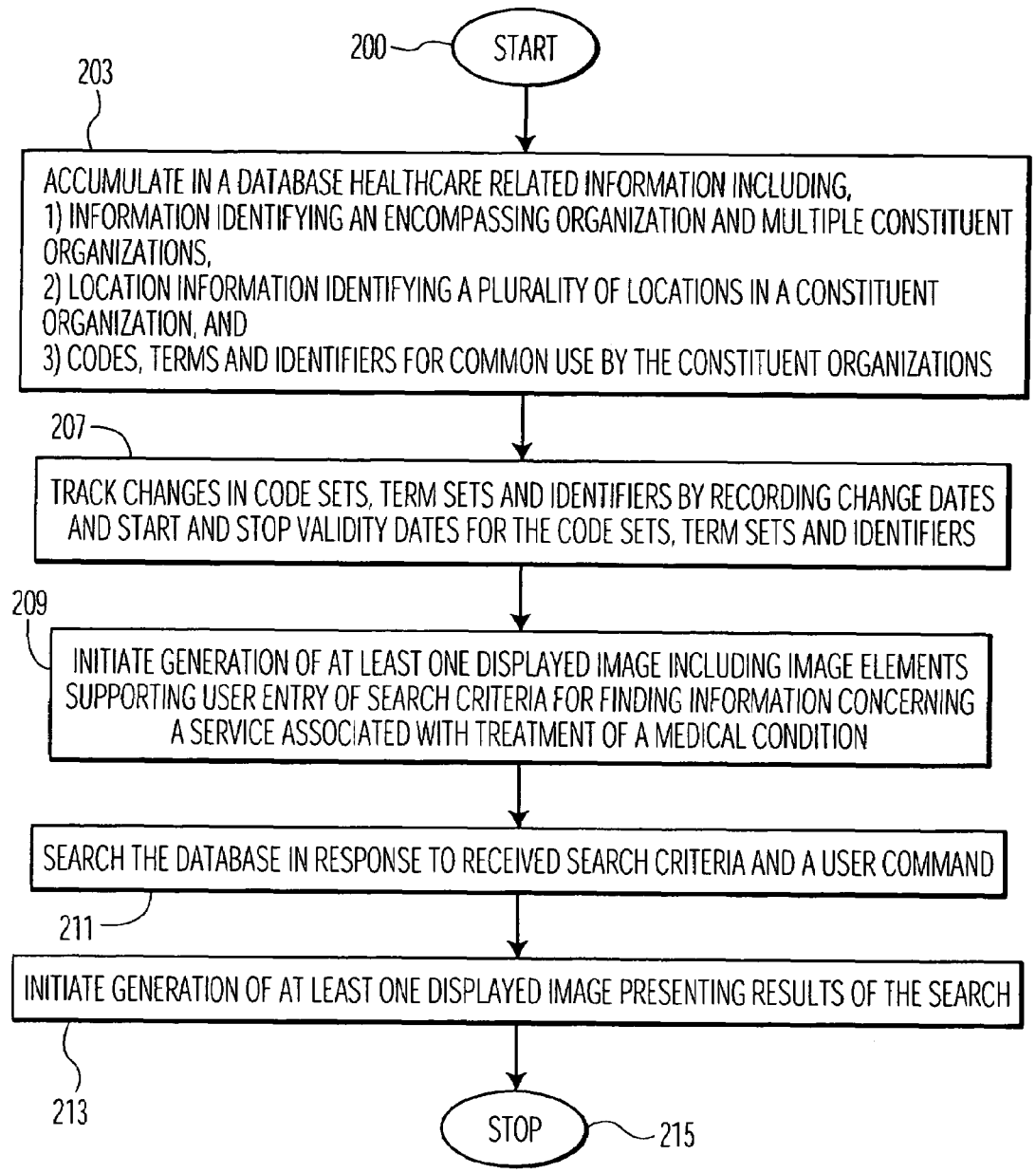
FIG. 2 shows a flowchart of a process employed by the information management system of FIG. 1 in searching, processing and presenting healthcare related information, according to invention principles.

FIG. 2 shows a flowchart of a process employed by application 15 of FIG. 1 in searching, processing and presenting healthcare related information derived from DB1. In step 203, following the start at step 200, application 15 accumulates within DB1 information derived from multiple sources. This information includes information identifying an encompassing organization and multiple constituent organizations and includes constituent organization type identifiers. A constituent organization type identifier identifies one or more of, a health care provider organization, a health care payer organization, a health care administration organization, a business organization or indicates a role of a constituent organization. Such a role indicator identifies an organizational relationship comprising a relationship between an individual involved in health care delivery and a health care service provider, a relationship between a creditor and a business organization or a relationship between a health care service provider and an organization including a location for hosting a patient encounter with a healthcare enterprise involving patient and healthcare enterprise interaction. The role indicator also identifies an organizational role such as, an employer, an issuer of identifiers for identifying items associated with a person, a payment guarantor, a creditor, a service provider and an organization hosting a patient encounter with a healthcare enterprise involving patient and healthcare enterprise interaction.

The accumulated DB1 information also includes location information identifying multiple locations in a constituent organization that are available to accommodate a patient for different purposes together with associated location type identifiers. The location type identifier identifies a particular location type such as a patient room, a hospital department room or a surgery related room or identifies location characteristics. Such location characteristics may indicate location facilities or a location characteristic of clinical significance influencing availability of a particular location to a patient having a particular medical condition. Other location characteristics include information identifying a function associated with a location, medical equipment available at a location or a billing code identifying a billing category of a location.

Figure 4:
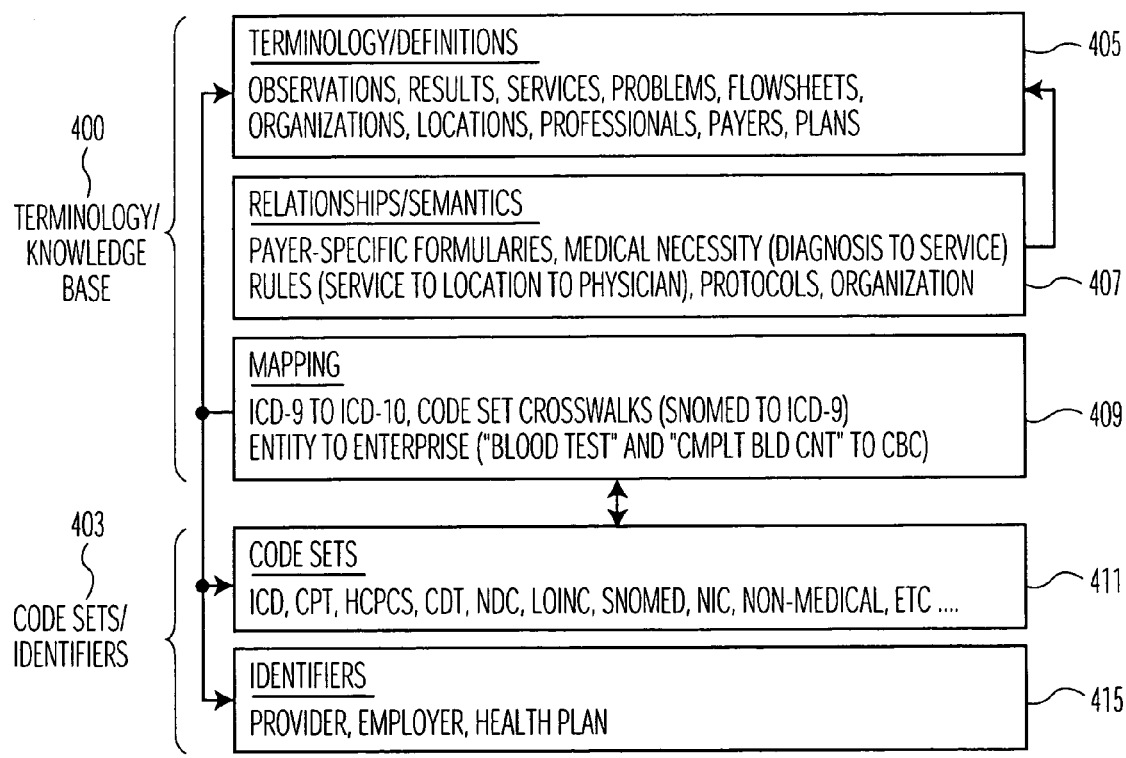
FIG. 4 shows a depiction of common information, codes, terms and identifiers centrally maintained in database 1 of FIG. 1, according to invention principles.

Application 15 also accumulates in DB1, codes, terms and identifiers for common use by constituent organizations as well as other terminology and information. FIG. 4 shows a depiction of the common information, codes, terms and identifiers centrally maintained in DB1 (and also maintained in DB2 in a similar structure) of FIG. 1. Information 400 maintained in DB1 includes terms and definitions 405 identifying clinical observations, clinical results, services, problems, flow sheets, treatment protocols and regimens, payers, physicians and health plans as well as the organization and location information previously described. DB1 further advantageously maintains relationships (including initiation and support data), business rules and constraints 407 sufficient to support dialog between a physician and a health insurer as well as dialog between health care providers. Dialog between a physician and a health insurer may be involved in a determination whether a proposed treatment procedure is medically necessary, for example. Dialog between health care providers may include communication of standard treatment protocols or regimens and involve clinical vocabulary hierarchies, for example. Relationship information 407 identifies relationships that exist between business objects (such as health provider organization, location, health professional, health service, payer and insurance plan). Relationship information 407 identifies an ownership hierarchy arrangement (e.g., a payer owning particular health care insurance plans or an organization owning other organizations). In addition, information 407 identifies simple affiliations (e.g., health professionals privileged to perform certain health services or health services that may be performed only at certain locations). Information 407 also identifies complex affiliations (e.g., a health plan that authorizes certain health provider organizations and health professionals to perform certain health services). A history of changes within a code set is maintained by DB1 to support historical data (e.g., deleted codes, time period of code validity etc.).

Mapping information 409 contains industry standard and other mapping information to support conversion between different versions of the same code set 403 and between different code sets 411 and identifiers 415. Code sets and identifiers 411 and 415 include HIPAA (Health Information Portability and Accountability Act) compatible code sets and other code sets used in a health care operation. Such code sets include, for example, ICD (International Classification of Diseases) codes, 9th Edition, Clinical Modification, (ICD-9-CM), Volumes 1, 2 and 3, as well as ICD-10 maintained and distributed by the U.S. Health and Human Services department. The code sets also include code sets compatible with HCPCS (Health Care Financing Administration Common Procedure Coding System), NDC (National Drug Codes), CPT-4 (Current Procedural Terminology), Fourth Edition CDPN (Code on Dental Procedures and Nomenclature). Further the code sets and terms include code sets compatible with SNOMED-RT "Systematicized Nomenclature of Medicine, Reference Terminology" by the College of American Pathologists, UMLS (Unified Medical Language System), by the National Library of Medicine, LOINC Logical Observation Identifiers, Names, and Codes Regenstrief Institute and the Logical Observation Identifiers Names and Codes (LOINC®) Committee, Clinical Terms also known as "Read Codes", DIN Drug Identification Numbers, Reimbursement Classifications including DRGs Diagnosis Related Groups. The code sets also include code sets compatible with CDT Current Dental Terminology, NIC (Nursing intervention codes) and Commercial Vocabulary Services (such as HealthLanguage by HealthLanguage Inc., by Apelon Inc.) and other code sets used in healthcare.

The common terminology accumulated in DB1 advantageously supports creating comparable and shareable data between different health care providers. This further enables the development of common guidelines, aggregate treatment outcomes analyses, and medical decision support rules for use by multiple organizations in a healthcare network. The common terminology includes an entry terminology, a reference terminology, and an administrative terminology. The entry terminology determines data formats for data entry, the reference terminology determines a data storage format and data structure and supports lexical mediation between terms and data fields, and the administrative terminology determines data structures suited for management and research. Application 15 supports lexical mediation, code, term and identifier mapping and information categorization using known categorization and description logic processing techniques. This type of processing involves logical relationship definition and automatic term classification and linkage. Such techniques are employed, for example, by an Apelon Inc. Description Logic based Ontylog product (www.Apelon.com).

Application 15 stores received code set, identifier and other information in DB1 using the data format in which the data is received. Application 15 also compiles description, edit rules, mapping information (for mapping between code set versions and different code sets) and other data relevant to codes and stores this data in DB1 in a data set associated with the corresponding code or code set. The compiled data set comprises standard attributes common to the majority (or all) of the employed code sets and identifiers, such as a limited 30 character description and fields able to accommodate differing edit rules, mapping information and other data. Application 15 in conjunction with DB1 also maintains an index providing a catalog (available to users via the Internet and other communication channels) of available information and code sets and identifiers including archived older versions of this data and identifying code set version or release, for example. This index identifies the DB1 inventory including the latest code sets and identifiers, older versions and includes code or code set description as well as, where data items are stored, their frequency of update and their source, for example. This index is used by application 15 in accessing and maintaining DB1 content. The archived data is retained as long as required. This may be determined by whether associated data exists in any data set in any distributed database such as DB2.

DB1 includes storage space allocated for future population with customer specific code sets and identifiers. The customer specific codes and identifiers may be installed upon download of DB1 content to a distributed database DB2 at an installation time or another update time, for example. Individual code sets and identifiers are themselves identified within DB1 (and DB2) by an allocated identifier (a primary key) used in providing the DB1 index and in DB1 data management and in maintaining a code set and identifier revision history including a deletion history. The primary key comprises a unique vendor or source internal number, plus code to identify the code set or identifier, for example.

DB1 is intermittently updated from external data sources (including distributed database DB2) via code set and identifier update cycles. For this purpose, DB1 stored code sets, identifiers and other stored information are internally associated (using the index) with external data sources and access communication data. The access communication data (IP address, URL etc.) including authorization codes and other security codes are employed by application 15 in bidirectionally communicating with the external sources to update DB1 content. Such update may be initiated by an external source or by DB1, in response to a data acquisition or request command or event, a periodic internal update command, a user command, or upon another condition such as a new installation or in response to detection of availability of a new code set version, for example. DB1 similarly initiates distribution of data to DB2 and other distributed databases upon similar commands and events. Application 15 thereby supports bidirectional communication and access by users to view DB1 content, to search for specific codes, to review a history of changes, or to download full copies or code set updates. Downloaded files may use a compressed, flat file type format, for example.

Application 15 creates a customized update file tailored to update requirements of a particular user database DB2. The customized update file contains the particular code sets, identifiers and other information required by a user and is prepared by application 15 for download to DB2 in response to initiation of a DB2 update cycle. Preferably a standard (e.g., XML compatible) update file is employed system wide or for multiple users. However, this may not be possible if the users have different system architectures and applications. Application 15 provides template update file formats including starter medical code sets, term sets and identifiers that may be selectable by a user as a customized update file. A customized update file may contain, for example, problem lists created from either or both ICD-9-CM and SNOMED for a particular user. Thereby, a user is able to create a list of allowable clinical problems based on standard medical code sets in a customized update file, for example.

In response to user command, application 15 in conjunction with DB1 also finds and incorporates externally sourced identifiers, such as national patient identifiers (e.g., Universal Patient Identification Numbers UPINs), in corresponding patient specific data. For this purpose, application 15 probabilistically matches patient demographic data in national identifier data sets such as the National Provider File (NPF), with demographic data in files in patient index and repository 37 (or in DB1 or DB2). Application 15 may similarly search physician national and local files for physician and patient identification codes and may also search for employer and health plan identifiers if national data sets are accessible. The results of the matching operation (and other data items) are processed by application 15 to provide a report file for access by a user via PCs 40 and 63 or for communication and storage.

Other information accumulated by application 15 in DB1 includes information identifying physicians associated with a location of a constituent organization, a professional specialty of physicians associated with a constituent organization, medical services available at a location of a constituent organization, medical services available to be provided by a particular physician at a location of a constituent organization, and medical conditions associated with treatment provided at a location of a constituent organization. Application 15 further accumulates in DB1 information identifying multiple healthcare companies, associated with a location of a constituent organization and responsible for payment of patient bills accrued under healthcare insurance plans.

In step 207 (FIG. 2), application 15 date and time stamps code sets, term sets and identifiers with a valid start date and end date. Application 15 also maintains a history of changes to the code sets, term sets and identifiers that identifies changed items and indicates date and time of change. Application 15 and DB1 uses the date and time stamps in supporting access and update of multiple versions of the same code set, term set and identifiers. This is advantageous during a transition phase when existing code sets are being replaced with different code sets and identifiers. This may occur during a transition to HIPAA compliant code sets, term sets and identifiers, or upon a payer acquiring the capability to use a new version of a code set, for example. In step 209, application 15 initiates generation of at least one displayed image including image elements supporting user entry of search criteria for finding information concerning a service associated with treatment of a medical condition. Other search criteria may be entered to find other data such as data concerning treatment associated with a medical condition and provided at a particular location of a particular constituent organization.

Figure 8:
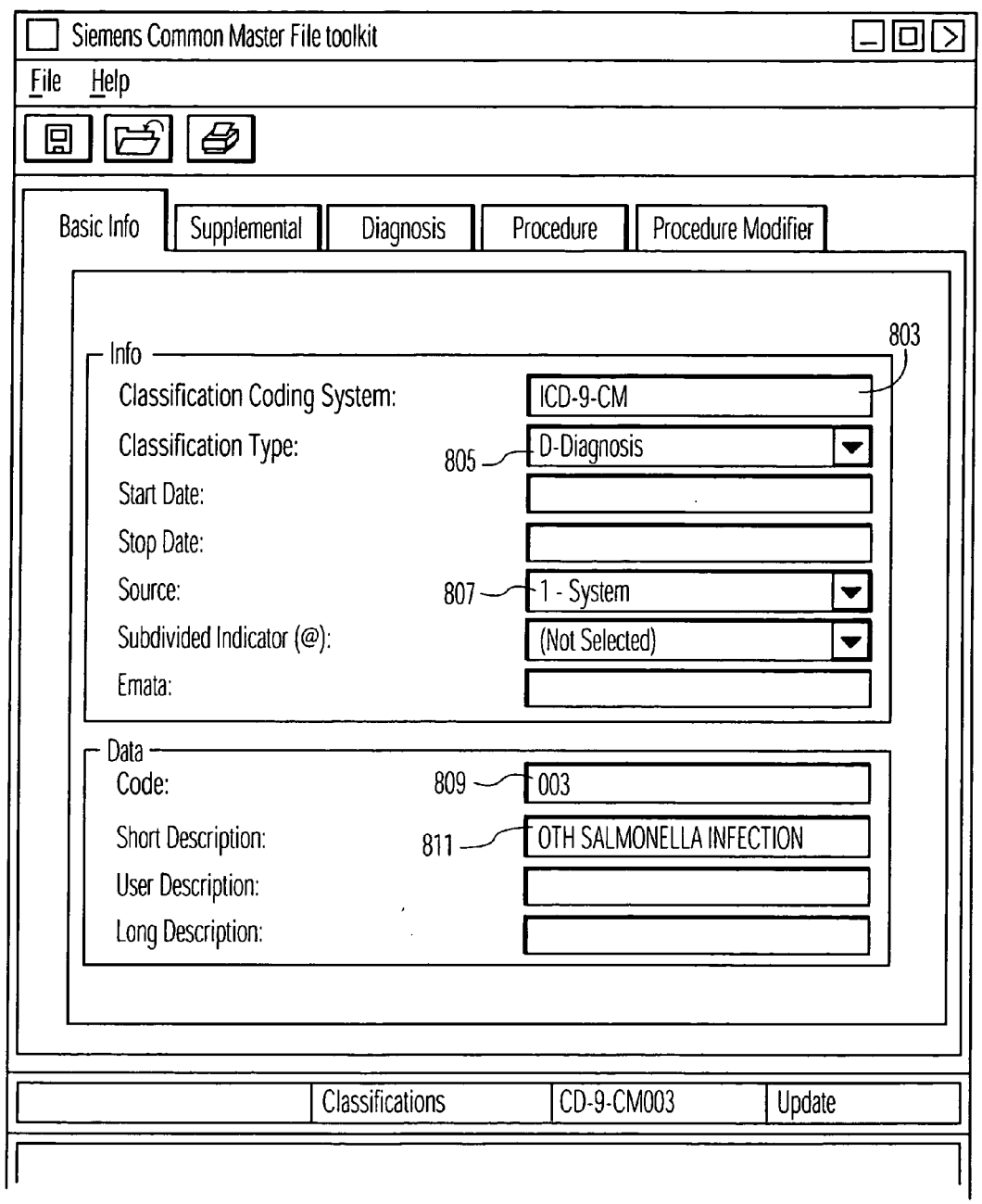
FIG. 8 shows a user interface display image supporting update and access to a database of multiple code sets, medical vocabularies and identifiers and other information, according to invention principles.

In step 211, application 15 searches DB1 in response to user command and the received search criteria. This involves mapping the received search criteria terms to corresponding different terminology using the stored codes, terms and identifiers to find a service used in treating a medical condition offered at a particular location by a particular organization. In step 211, application 15 initiates generation of at least one displayed image presenting results of the search. Thereby DB1 facilitates identification of a service associated with treatment of a particular medical condition and offered at a location of a constituent organization, for example. The process of FIG. 2 is complete at step 215. FIG. 8 illustrates a user interface display image supporting update and access to a database of multiple code sets, medical vocabularies and identifiers and other information. Specifically, FIG. 8 shows use of a Web based maintenance form to update an ICD-9-CM code classification in DB1. Updated elements include classification type 805, source 807, code 809 and description 811.

Figure 3:
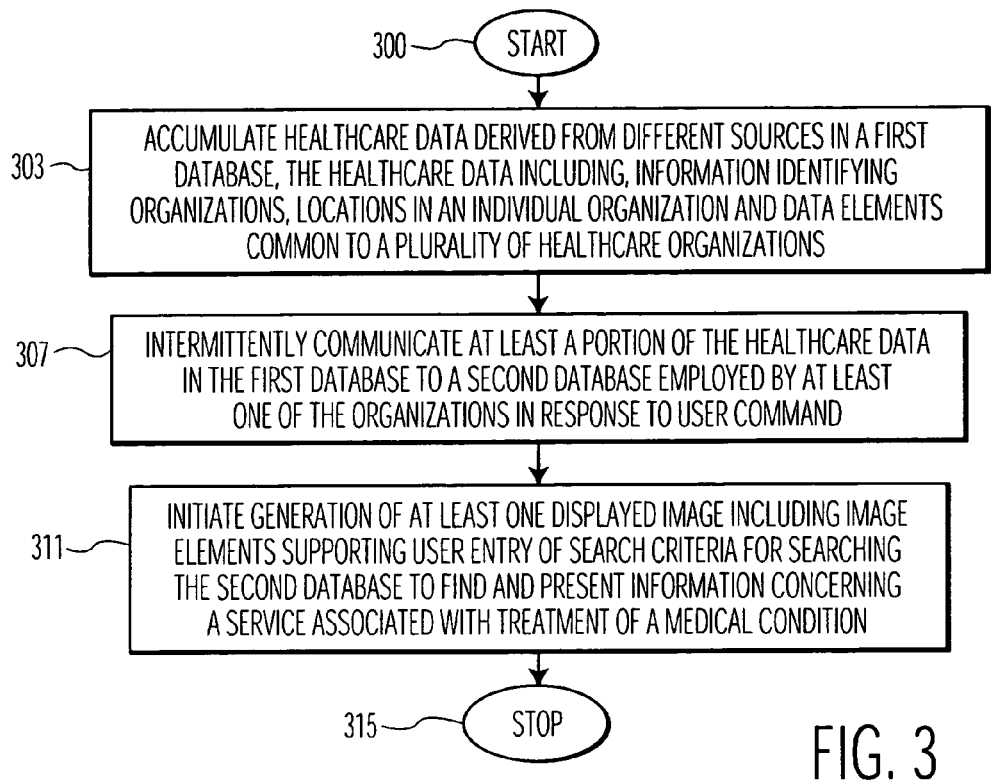
FIG. 3 shows a flowchart of a process employed by the information management system of FIG. 1 in accumulating, distributing and processing healthcare related information between hierarchically organized databases, according to invention principles.

FIG. 3 shows a flowchart of a process employed by the information management system of FIG. 1 in accumulating, distributing and processing healthcare related information between hierarchically organized databases DB1 and DB2. The healthcare data in DB1 is centrally maintained by an encompassing organization (e.g., a healthcare network) to serve constituent organizations maintaining individual healthcare databases such as DB2. In step 303, following the start at step 300, application 15 accumulates within DB1 information derived from multiple sources. This information, as previously explained in connection with step 203 of FIG. 2, includes information identifying organizations and their characteristics as well as locations in organizations and their associated characteristics together with codes, terms, identifiers and other information for common use by the organizations. In step 307, application 15 intermittently communicates at least a portion of the healthcare data in centrally maintained DB1 to DB2 in response to user command. In an alternative embodiment, this information distribution may be initiated periodically, upon detection of a change in stored data, or upon an update request or command from a requesting application or in response to another indication that DB2 is to be updated.

Figure 6:
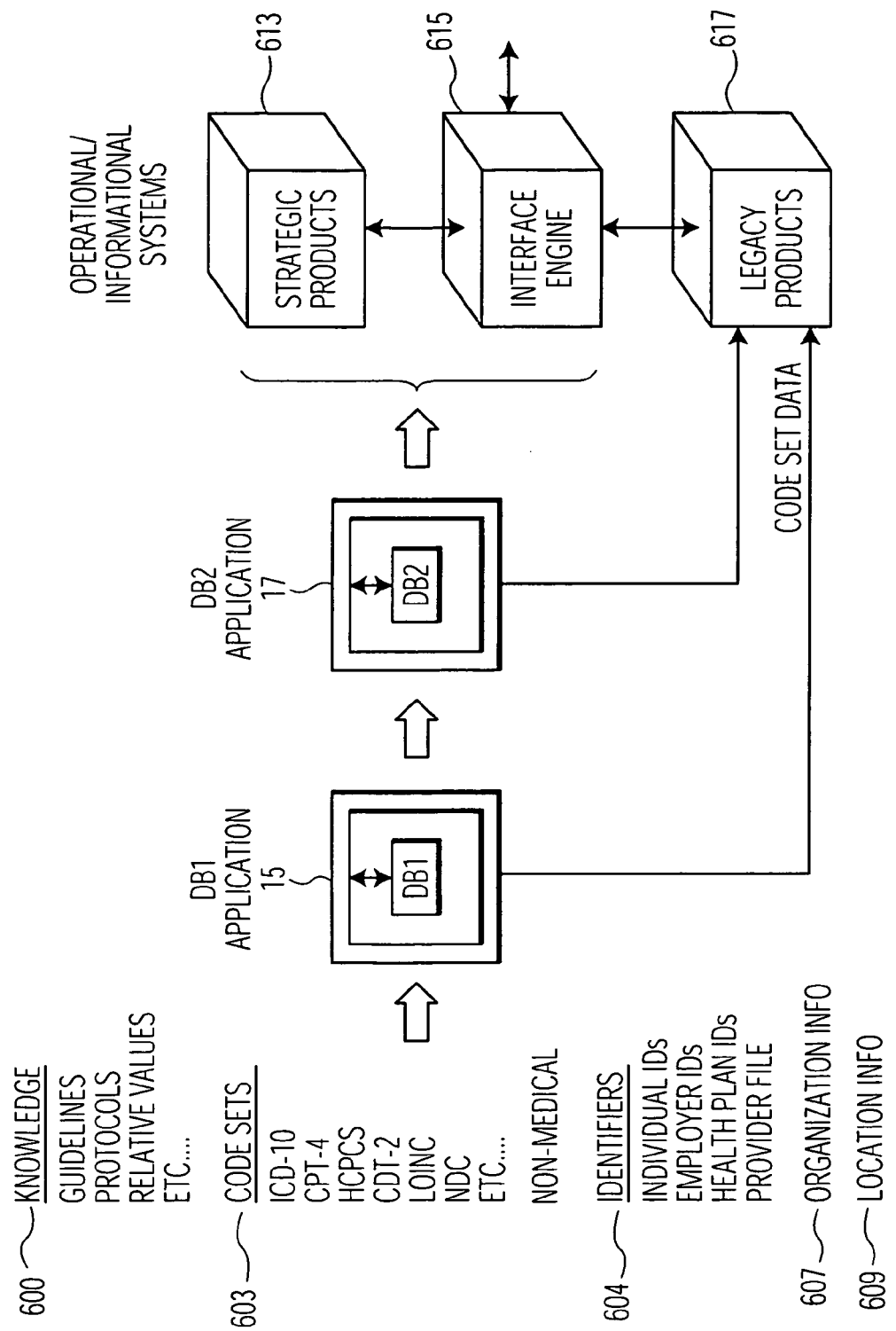
FIG. 6 shows a hierarchically organized database system used in accumulating, processing and distributing healthcare related information including organization and location related information as well as common codes, terms and identifiers, according to invention principles.

FIG. 6 illustrates the hierarchically organized database system used in accumulating, processing and distributing healthcare related information including organization and location related information as well as common codes, terms and identifiers, from DB1 to DB2. The distributed information includes medical and non-medical codes and terms 603, identifiers (e.g., individual, employer, health plan and provider identifiers) 604, other information (including treatment guidelines, protocols, values and business rules) 600 as well as organization information 607 and location information 609. Treatment guidelines as used herein comprise best or effective medical practice information authored by a recognized medical authority concerning determination and administration of treatment to a patient to address one or more identified medical conditions. A protocol as used herein is a schedule of discrete tasks to be performed that are associated with a treatment regimen that addresses a particular medical condition. A business rule as used herein comprises policies, processes and procedures used by an organization to implement and support delivering healthcare to a patient. The information in DB2 is used by operational and information systems 613 and 617 employed by a constituent organization of an encompassing health network organization. Other products 617, employed by the constituent organization, use information from DB2 as well as information directly from DB1. Operational and information systems 613 and 617 may use information in a format provided by DB2 (or DB1). Systems 613 and 617 may also require such information to be in a format tailored to their requirements. For this purpose, interface processor 615 collates, transforms, validates and transfers information (including codes, terms and identifiers) from DB2 into a file or other format required by systems 613 and 617. Interface processor 615 incorporates code, term and identifier translation capability and uses a standard Electronic Data Interchange transaction interface (using American National Standards Institute (ANSI) X12 standards) which supports validation of transferred data. Interface processor 615 performs additional validity checks to verify that a correct code, term or identifier is being used in a data transfer to systems 613 and 617. In an alternative embodiment a different interface may also be employed.

Figure 7:
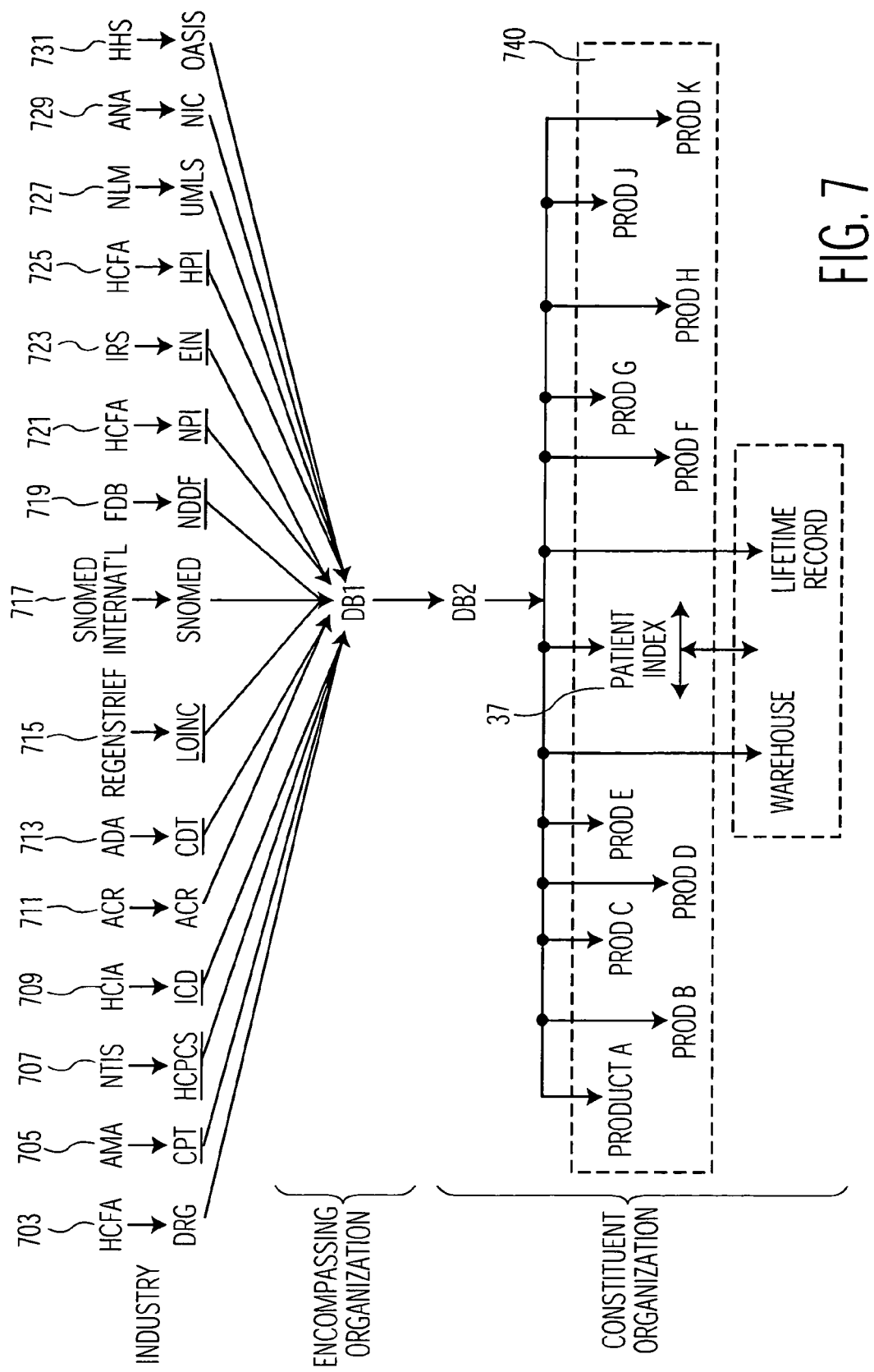
FIG. 7 shows processing of multiple code sets, medical vocabularies and identifiers for distribution in a hierarchically organized database system, according to invention principles.

FIG. 7 shows processing of multiple code sets, medical vocabularies and identifiers for distribution in a hierarchically organized database system. Specifically, code sets, terms and identifiers 703-731 managed by particular corresponding responsible institutions and used in the medical industry are incorporated in DB1 of an encompassing health network organization for distribution to DB2 of a constituent organization. The code set information 703-731 and associated mapping information is used by application 17 and interface processor 615 (FIG. 6) in supporting business applications and information systems 613 and 617 representing products 740 (FIG. 7). The information is further used in accessing clinical record repository 37 (including patient lifetime clinical record and electronic patient record systems) and in data warehousing. The code sets, terms and identifiers 703-731 include for example Diagnostic Related Groups (DRG) 703 managed by the Health Care Financing Administration (HCFA), Current Procedural Terminology (CPT) 705 managed by the American Medical Association (AMA), the Health Care Financing Administration Common Procedure Coding System (HCPCS) 707 managed by the National Technical Information Service (NTIS), for example.

The connection of a new operational system to DB2 may require transformation of an initial standard database download file into a data format compatible with the new operational information system. Subsequently, additions or deletions to the code sets, terms and identifiers (as well as associated standard descriptive data) used by an operational system are applied to DB1 or DB2 information and are not made to the operational system files. This advantageously enables DB1 to be made a single point of maintenance.

DB2 is structured in a similar manner to DB1 (as described in connection with FIG. 4) to facilitate bidirectional data transfer between them. However DB1 and DB2 in another embodiment may be differently structured. Further, DB2 may contain all, or a subset of, the information in DB1 comprising a core set of codes, terms, identifiers and information relevant to the constituent organization operation and derived and updated from DB1 to maintain consistency with other constituent organization operations served by DB1. DB2 also includes information tailored to the specific requirements of its host constituent organization including updates applied by the constituent organization to implement changes before they are generally available. Updates to code sets are typically published periodically, but use of new medical technology may require the use of new codes before they are formally available from the source concerned. DB2 also contains supplemental local codes (e.g., HCPCS level III) and local identifiers (e.g., residents and interns not formally having a National Provider Identifier) relevant to the constituent organization and the business entities it interacts with (e.g., health plans). If these codes and identifiers are generally used, they may be communicated by application 17 from DB2 to application 15 for incorporation in DB1 for use particular payers in particular geographic regions, for example.

The system incorporates in DB2 a core set of codes terms and identifiers common to multiple organizations in a health network together with user specific (i.e., specific to a constituent organization) codes terms and identifiers to form a hybrid vocabulary supporting the business policies, operations and procedures of the user. Such operations may employ, a tailored set of constituent organization specific clinical problems created from a mix of code sets, a tailored set of available medical services created from multiple predetermined service sets as well as a tailored set of treatment protocols and regimens created from a selected set services and problems, for example. DB2 also defines linkages within the DB2 vocabulary, including code sets and identifiers that link the vocabulary elements with available health services, treatment protocols and regimens and health plans, for example. DB2 (in similar fashion to DB1) maintains relationships, business rules and constraints sufficient to support dialog between a physician and a health insurer as well as dialog between health care providers. Such dialog supports determination of whether a proposed treatment procedure is medically necessary, for example. The relationship linkages maintained by DB2 mirror those previously described for DB1 in connection with FIG. 4.

Application 17 advantageously filters data from DB1 prior to storing the filtered information in DB2 using predetermined filter information. The predetermined filter information ensures that filtered healthcare data for storage in DB2 matches the business processes and services provided by the constituent organization maintaining and using DB2. The filter ensures that data supporting a business process or service matches constituent organization requirements. The filter ensures healthcare data stored in DB2 supports not just an order for performance of a service (such as an order for a lumber puncture to be performed), but also the additional services performed by the constituent organization in performing the service (such as additional discrete services addressing resource allocation, costing, and billing for the lumber puncture), for example.

DB2, in similar fashion to DB1, includes mapping information for mapping a term, code or identifier in a first set of healthcare data to a different corresponding term, code or identifier in a second set of said healthcare data. The mapping information supports conversion between different versions of the same code set and between different code sets (411 FIG. 4) and identifiers (415 FIG. 4). The mapping information also supports conversion of user-defined synonyms, and constituent organization customer vocabulary to standard or recognized values. The DB2 mapping information supports conversion of individual user specific identifiers, terms and codes to corresponding standard codes, identifiers, or terms defined for use by a constituent enterprise. Further, updated information is also communicated by DB2 to update DB1. Such communication is initiated in response to similar conditions as are used to initiate download of information from DB1 to DB2 described in connection with FIG. 2.

Continuing with FIG. 3, in step 311, application 17 initiates generation of at least one displayed image including image elements supporting user entry of search criteria for finding information concerning a service associated with treatment of a medical condition, for example. FIG. 5 shows a user interface display image menu including window 900 supporting such a user search for a service. A user may enter criteria including one or more of organization 908, location 902, type 906, category 904 and gender association 913, for example and application 17 (FIG. 1) initiates a search of DB2 using the centrally maintained common codes, terms and identifiers in DB2. The search is initiated in response to user activation of button 925 and the search results are displayed in window 920. Details concerning a user selected search result element (e.g., 304A) are displayed in display box 923. Similar user interface images in conjunction with web browser applications provide a user with Web access to view DB2 (or DB1) content, to search for specific codes, to review a history of changes, or to download full copies or incremental updates of DB2 information in a user selectable (e.g., flat or compressed) data format. The process of FIG. 3 ends at step 315.

The systems, processes and user interface display formats presented in FIGS. 1-9 are not exclusive. Other systems, processes and user interface forms may be derived in accordance with the principles of the invention to accomplish the same objectives. The inventive principles may be applied in a variety of environments for identifying and tracking service, location and organization related information and in supporting executable applications of an organization using common sets of codes terms and identifiers. The inventive principles are not constrained to be used in the healthcare field. Specifically, the inventive principles and use of a common vocabulary management system may be applied in any environment where multiple terminologies exist and where operations are facilitated by providing a managed common reference terminology.

What is claimed is:

1. A system for managing healthcare related information supporting operation of a healthcare enterprise, comprising:
   a first database including healthcare data derived from a plurality of different sources, said healthcare data including
   (a) information identifying a plurality of organizations,
   (b) location information identifying a plurality of locations in an individual organization available to accommodate a patient for different purposes, and
   (c) data elements common to a plurality of healthcare organizations, the common data elements comprising healthcare data codes, terms and identifiers and supporting use of consistent terminology between said plurality of organizations said healthcare data codes, terms and identifiers support identifying a medical condition and an associated service provided at a location of an organization; and a processor for intermittently receiving healthcare data update data sets to update said codes, terms and identifiers in said first database and for providing at least a portion of said update data sets including healthcare data codes, terms and identifiers in said first database to a second database employed by at least one of said plurality of organizations in response to user command, said second database also supporting user access to selectable items of healthcare data codes, terms and identifiers.

2. A system according to claim 1, including an interface processor for intermittently receiving healthcare data updates for incorporation in said first database and for intermittently providing at least said portion of said healthcare data in said first database to said second database.

3. A system according to claim 1 including a tracking processor for date stamping at least one of, code sets, term sets and identifiers with a date of validity including at least one of, (a) a valid start date and (b) a validity end date.

4. A system according to claim 1 including a tracking processor for maintaining a history of changes to at least one of, code sets, term sets, identifiers, treatment guidelines, treatment protocols and business rules for use in identifying an item changed and an associated date of change.

5. A system according to claim 1, wherein said first database includes terms specific to a particular organization, the specific terms supporting business operation of said particular organization.

6. A system according to claim 1, including a mapping processor for mapping a term in a first code set of said healthcare data to a different corresponding term in a second code set of said healthcare data.

7. A system according to claim 1, wherein said first database includes, an organization type identifier identifying a type of organization and a location type identifier identifying a location type of a location in an individual organization.

8. A system according to claim 1, wherein said first database incorporates information identifying at least one of, (a) physicians associated with a location in an individual organization, (b) a professional specialty of a physician associated with an organization, (c) medical services available at a location in an individual organization, (d) medical services available to be provided by a particular physician at a location in an individual organization, and (e) a plurality of medical conditions associated with treatment provided at a location of an organization.

9. A system according to claim 1 wherein said plurality of organizations comprise a plurality of healthcare companies responsible for payment of patient bills accrued under healthcare insurance plans, said healthcare companies being associated with a location of an organization.

10. A system according to claim 1 including a collation processor for collating data items of said portion of said healthcare data to provide collated healthcare data to said second database.

11. A system according to claim 1 including a filter for filtering said portion of said healthcare data to provide filtered healthcare data to said second database.

12. A method for supporting user access to healthcare data, comprising the steps of:

generating of at least one displayed image including image elements supporting user entry of search criteria for finding information concerning a service associated with treatment of a medical condition;

searching a electronic first database in response to user command and receiving said search criteria, said first electronic database incorporating healthcare data intermittently provided by a electronic second database, said healthcare data including, (a) information identifying a plurality of organizations, (b) location information identifying a plurality of locations in an individual organization, and (c) data elements common to a plurality of healthcare organizations, the common data elements comprising codes, terms and identifiers and supporting use of consistent terminology between said plurality of organizations said codes, terms and identifiers enabling identifying a medical condition and an associated service provided at a location of an organization;

intermittently receiving healthcare data update data sets derived from said first database to update said codes, terms and identifiers in said second database; and generating at least one displayed image presenting results of said search.

* * * * *